United States Patent [19]

Fujioka et al.

[11] Patent Number: 4,950,234
[45] Date of Patent: Aug. 21, 1990

[54] DEVICE FOR ADMINISTERING SOLID PREPARATIONS

[75] Inventors: Keiji Fujioka, Amagasaki; Nobuhiko Tamura, Toyonaka; Yoshihiro Takada, Takatsuki; Kenji Himeshima, Toyonaka, all of Japan

[73] Assignees: Sumitomo Pharmaceuticals Company, Limited; Nissho Corporation, both of Osaka, Japan

[21] Appl. No.: 198,290

[22] Filed: May 25, 1988

[30] Foreign Application Priority Data

May 26, 1987 [JP] Japan .................. 62-129439
May 26, 1987 [JP] Japan .................. 62-79259[U]

[51] Int. Cl.$^5$ ............................................. A61M 5/18
[52] U.S. Cl. .................................... 604/60; 604/218; 604/122
[58] Field of Search .................. 604/51, 57, 59, 60, 604/62, 218, 122, 283

[56] References Cited

U.S. PATENT DOCUMENTS

| 2,009,393 | 7/1935 | Failla ........................ 604/60 |
| 2,761,446 | 9/1956 | Reed . | |
| 3,469,579 | 9/1969 | Hubert ........................ 604/283 |
| 3,506,008 | 4/1970 | Huck ........................ 604/60 |
| 3,744,493 | 7/1973 | Booher et al. . | |
| 3,802,433 | 4/1974 | Raven ........................ 604/283 |
| 3,828,987 | 8/1974 | Drummond et al. ........................ 604/208 |
| 4,402,308 | 9/1983 | Scott . | |
| 4,451,253 | 5/1984 | Harman . | |
| 4,755,173 | 7/1988 | Konopka et al. ........................ 604/122 |
| 4,774,091 | 9/1988 | Yamahira et al. ........................ 604/60 |
| 4,790,819 | 12/1988 | Li et al. ........................ 604/49 |

FOREIGN PATENT DOCUMENTS

| 0044293 | 6/1931 | Denmark ........................ 604/59 |
| 0255123 | 2/1988 | European Pat. Off. . | |
| 0252587 | 6/1926 | United Kingdom ........................ 604/60 |
| 821087 | 9/1959 | United Kingdom . | |

Primary Examiner—Stephen C. Pellegrino
Assistant Examiner—Denise W. DeFranco
Attorney, Agent, or Firm—Birch, Stewart, Kolasch & Birch

[57] ABSTRACT

A device for administering solid or semisolid preparations in an organism subcutaneously. The equipment comprises a barrel having a nozzle for attachment of a hollow needle, a plunger slidably arranged in the barrel and is used in combination with a guide member adapted to be snugly accommodated within the lumen of the barrel. The solid preparations are generally housed in the guide member and/or needle and forced into the body subcutaneously through the needle.

12 Claims, 3 Drawing Sheets

DEVICE FOR ADMINISTERING SOLID PREPARATIONS

FIELD OF INVENTION

This invention relates to a device for administering solid or semisolid preparations subcutaneously to layers of a patient.

BACKGROUND OF THE INVENTION

In the past, subcutaneous implantation of solid preparations in the body has required surgery that takes a lot of labor and is accompanied by physical and mental sufferings and, occasionally, a surgical scar.

To solve such problems, some of the inventors have recently proposed a device for administering solid or semisolid preparations in the body through the skin, for example, in EP-A-139286 and Japanese patent applications laid-open Nos. 60-227772, 60-129057, 61-79470, 61-82761 and 61-180400. Such a device generally comprises a hollow needle and a plunger slidably arranged in the needle and, makes it possible to inject solid or semisolid preparations in the subcutaneous layers of a patient without performing any surgical operation. However, such a device makes it difficult to aseptically administer solid or semisolid preparations in the body.

To solve such a problem, the above inventors have proposed, in Japanese application Nos. 61-180398 and 61-180399 (corresponding to U.S. patent application Ser. No. 70429 and EP 87 11 0993), use of a device for subcutaneous implantation of solid preparations that comprises a hollow barrel with a capsule chamber, a hollow needle attached to the tip of the barrel, and a plunger slidably arranged in the barrel. Such a device may be used in combination with capsules containing solid or semisolid preparations and, the preparations are first ejected from the capsule by the plunger and then injected into the subcutaneous layers through the needle. Thus, such a device makes it possible to implant solid or semisolid preparations aseptically, but it also has some problems awaiting a solution. For example, when loading the capsule into the barrel, the operator is required to focus his concentration on an opening of the capsule chamber because of its small diameter. In addition, such a device requires prudent care to prevent the plunger from bending or breaking since the plunger is occasionally caught in the barrel.

SUMMARY OF THE INVENTION

It is therefore an object of the present invention to provide a device for administering solid or semisolid preparations in the body, which is simple to handle and makes it possible to aseptically handle solid or semisolid preparations during subcutaneous implantation.

Another object of the present invention is to provide a device for administering solid or semisolid preparations in the body, which makes it possible to administer solid or semisolid preparations in the subcutaneous layers of the skin easily and smoothly.

According to the present invention, there is provided a device for administering solid or semisolid preparations in an organism subcutaneously, comprising a barrel having a nozzle for attachment of a hollow needle, and a plunger slidably arranged in the barrel, said plunger comprising a plunger body of an outside diameter equal to or slightly smaller than the inside diameter of said barrel, and an elongated, small-sized rod portion, connected to the tip of the plunger body, of an outside diameter equal to or slightly smaller than the inside diameter of said needle, the length of said small-sized rod portion being so designed that the tip of the rod portion protrudes for a certain distance beyond the tip of the needle when said plunger is forced into the barrel until said plunger body reaches its innermost position.

The device of the present invention is used in combination with a guide member adapted to be contained within the barrel. The guide member is provided with a funnel-shaped guide hole to facilitate insertion of the small-sized rod portion of the plunger into the lumen of the needle. The guide hole includes a tapered guide portion and an elongated straight portion extending from the small end of the tapered guide portion to the tip of the guide member. The guide member is designed to have an outside diameter slightly smaller than the inner diameter of the barrel though the size and configuration of the guide member may be varied to suit specific requirements. The front part of the guide member may be tapered to fit with a tapered front inner wall of the barrel.

To ensure aseptic handling of the solid or semisolid preparations, it is preferred to use such a guide member as a capsule for solid or semisolid preparations. In this case, the guide hole of the guide member containing one or more preparations is sealed by a film of a biocompatible material at the tip end of the guide member and a cap at the opposite end to give a hermetically sealed encapsulation.

In a preferred embodiment of the present invention, there is provided a device for administering solid or semisolid preparations in an organism subcutaneously, comprising a barrel having a nozzle for attachment of a hollow needle, a plunger slidably arranged in the barrel, and a guide member adapted to be snugly accommodated within the lumen of the barrel, said guide member having an outside diameter slightly smaller than the inside diameter of the barrel and being provided with a funnel-shaped guide hole, said plunger comprising a plunger body of an outside diameter equal to or slightly smaller than the inside diameter of said barrel, and an elongated, small-sized rod portion of an outside diameter equal to or slightly smaller than the inside diameter of said needle, said small-sized rod portion being connected to the tip of the plunger body and having a length equal to or slightly smaller than the distance from the rear end of the guide member to the tip of the needle. In this, the guide member is loaded into the barrel so that it comes into contact with the front inner wall of the barrel, and the small-sized rod portion of the plunger is designed to have a length corresponding to the distance from the needle point to the rear end of the guide member loaded in the barrel. Thus, when the plunger is forced into the barrel loaded with the guide member until the tip end of the large-sized slide portion of the plunger comes into contact with the rear end of the guide member, the tip end of the small-sized slide portion of the plunger is stopped in the area within the edge portion of the needle.

In another preferred embodiment, the needle is provided with an air hole through which air in the barrel and the needle is discharged when the plunger is forced into the barrel. The needle may be attached to the tip of the barrel in any way. For example, if the needle is a cylindrical hollow tube with no hub, the needle is inserted into and fixed to the nozzle with an adhesive. In this case, the needle is so designed that it has an outside diameter equal to the inside diameter of the nozzle. If the needle is provided at its one end with a hub, the needle is attached to the barrel by inserting the nozzle of the barrel in the hub of the needle.

In the solid preparation administering equipment of the present invention, the guide member containing at least one solid or semisolid preparations is loaded from its front part into the barrel through the rear opening of the barrel and, the preparations in the guide member are injected into the body through the hollow needle by forcing the plunger into the barrel until the tip end of the large-sized slide portion comes into contact with the rear end of the guide member. Thus, the device of the present invention may hereinafter be called "a solid preparation injector".

The invention will be further apparent from the following description taken in conjunction with the accompanying drawings which show, by way of example only, preferred embodiments thereof.

PREFERRED EMBODIMENT OF THE INVENTION

Figure 1:
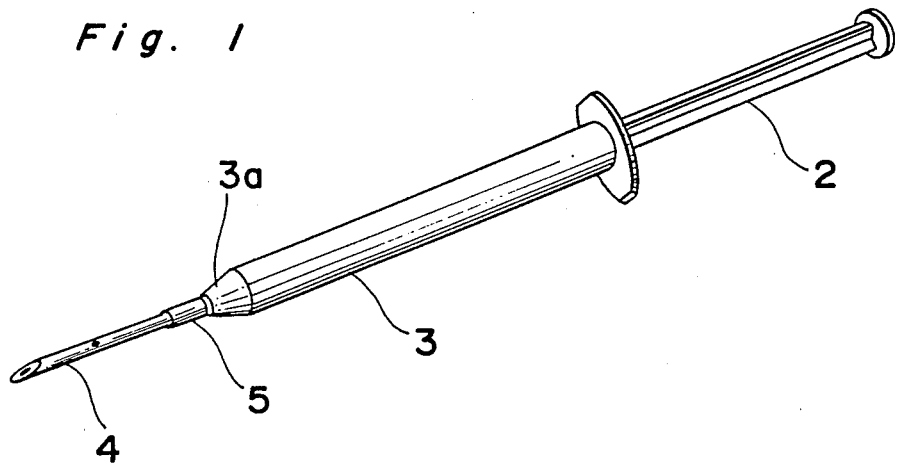
FIG. 1 is a perspective view of a solid preparation injector embodying the present invention.
Figure 2:
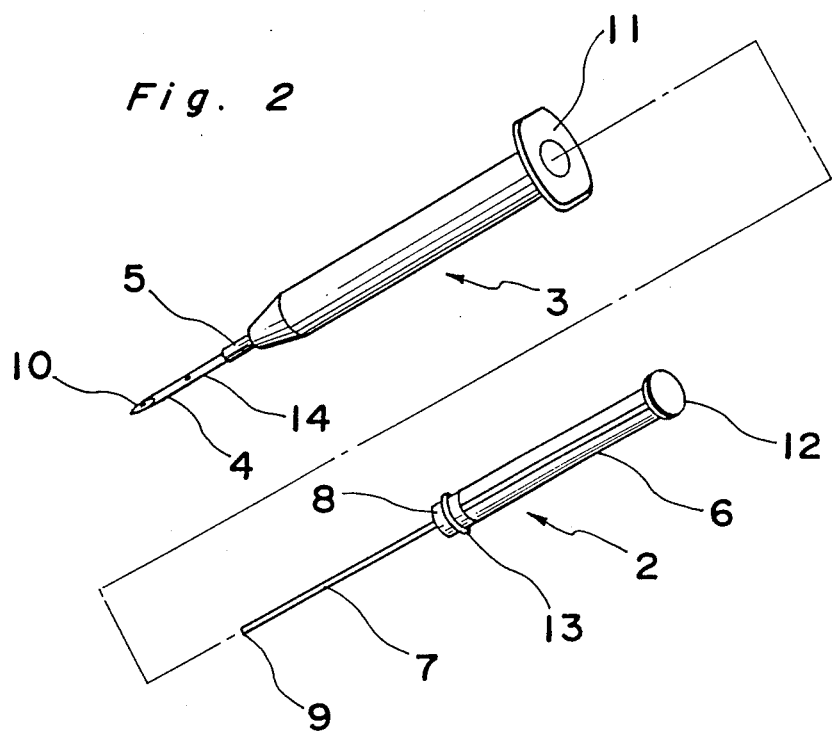
FIG. 2 is an exploded perspective view of the injector of FIG. 1.

Referring now to the figures, there is shown a solid preparation injector embodying the present invention, comprising three basic components, i.e., a barrel 3, a plunger 2 slidably arranged in the barrel 3, and a hollow needle 4 attached to said nozzle 5 of the barrel 3.

The barrel 3 is provided at its one end with a nozzle 5 for attachment of a hollow needle 4 and, at the other end, with a flange 11 which serves as a support for the device to force the plunger into the barrel. The barrel 3 has a uniform inside diameter through its entire length except for the tip end 3a that is tapered inwardly. The tapered inner wall of the tip end 3a serves as a seat for a guide member mentioned below.

As a material for the barrel, there may be used those such as glasses, metals and synthetic resins. It is, however, preferred to use a transparent material such as glasses and synthetic resins. The transparent synthetic resin includes, without being limited to, polypropylene, polystyrene, polymethyl pentene, stylene-acrylonitrile copolymers. The barrel of such a transparent material makes it possible to observe loaded conditions of the guide member 15 and/or conditions of the solid preparation at the time of loading and administration.

The needle 4 is bevelled at its one end to form a pointed tip, or an edge 10. The needle 4 is provided with an air hole 14 away from the edge 10 to prevent air in the barrel from being injected into the body through the needle 4 when implanting the solid preparations 16 into the body. The air hole 14 is generally formed at a distance of not less than 5 mm, preferably, 10 to 20 mm from the edge 10 of the needle 4 so that the hole 14 is prevented from sinking into the subcutaneous layers when the needle 4 has been stabbed into the subcutaneous layers. The needle 4 is generally designed to be 0.5 to 3 mm in inside diameter and not less than 20 mm in length. The length of needle varies with scope of applications, but usually ranges from 25 to 60 mm. The needle 14 may be made of any material, provided that it is not corroded by chemicals and has a mechanical strength sufficient to prevent the needle from breaking or bending during insertion and withdrawal. It is, however, preferred to use a stainless steel as a material for needle. The hollow needle 4 is press-fitted into the nozzle 5 of the barrel 3 and fixed thereto with an adhesive.

The plunger 2 is composed of a plunger body 6 and an elongated, small-sized rod portion 7 connected at its one end to the tip of the plunger body 6. The plunger body 6 is of a cross-shaped section and is integrally molded with a flange 12. The plunger body 6 also includes a large-sized slide portion 8 to be engaged with an inner wall of the barrel 3. The large-sized slide portion 8 has a diameter nearly equal to the inside diameter of the barrel 3. Preferably, the large-sized slide portion 8 is provided with a ring-like gasket 13 of a rubberlike elastic material to allow the plunger body 6 to move smoothly. The elastic material for the ring-like gasket 6 includes, without being limited to, butyl rubber and silicone rubber. However, if the needle 4 attached to the nozzle 5 has no air hole, it is preferred that the plunger has no gasket and is provided at its large-sized slide portion 8 with one or more grooves extending in the direction parallel to the center axis of the plunger body 6.

As a material for the body member 6, there may be used those such as glasses, metals and synthetic resins. It is preferred to use synthetic resins such as polypropylenes, polystyrenes and the like.

The small-sized rod portion 7 is a rodlike component, preferably, of stainless steel and fixed to the tip of the plunger body 6. The small-sized rod portion 7 is designed to have a diameter equal to or smaller than the inner diameter of said needle; and its length is so determined that the tip 9 of the small-sized rod portion 7 protrudes for the determined distance beyond the edge 10 of the needle 4 when the plunger 2 is forced into the barrel 3 until the plunger body 6 reaches its innermost position, at which the tip end of the plunger body 6 comes in contact with the tapered inner wall of of the barrel 3. In other words, the length of the small-sized rod portion 7 is determined by the lengths of the needle 4, nozzle 5 and a guide member 15 and a distance between the tip 9 of the guide member 15 and the rear end of the needle 4. Thus, when the plunger 2 is fitted in the barrel 3 with the guide member 15 and then forced into the barrel 3 until the tip of the large-sized slide portion 8 comes into contact with the rear end of the guide member 15, the tip of the small-sized rod portion 7 is located in the area within the edge 10 of the needle 4.

Figure 5:
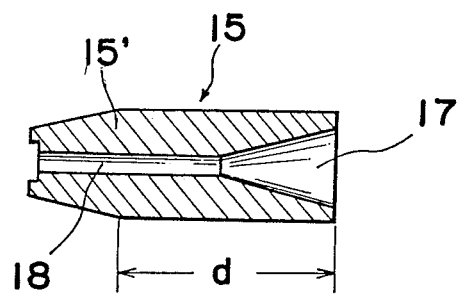
FIGS. 5 to 8 are cross sections showing various configurations of a guide member or capsule embodying the present invention.

As noted previously, the solid preparation injector 1 is used in combination with the guide member 15. As shown in FIG. 5, the guide member 15 is a hollow body 15' with a funnel-shaped guide hole composed of a tapered guide portion 17 and an elongated straight portion (hereinafter referred to lumen) 18 extending from the small end of the tapered guide portion 17 to the tip of the guide member 15. The guide member 15 has an outside diameter slightly smaller than the inner diameter of the barrel 3 and is tapered at its front part to make it fit the tapered inner wall of the barrel 3.

Figure 7:
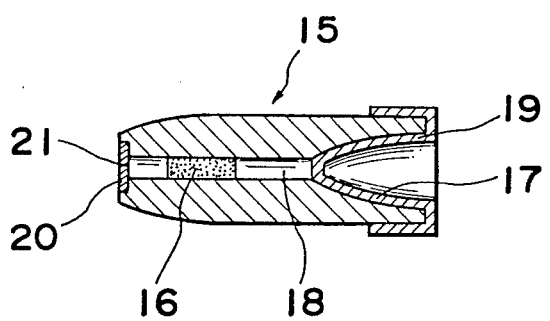
Figure 8:
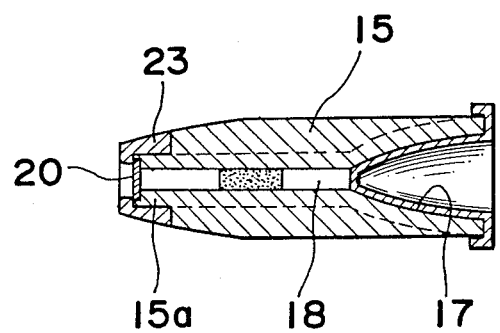
Figure 9:
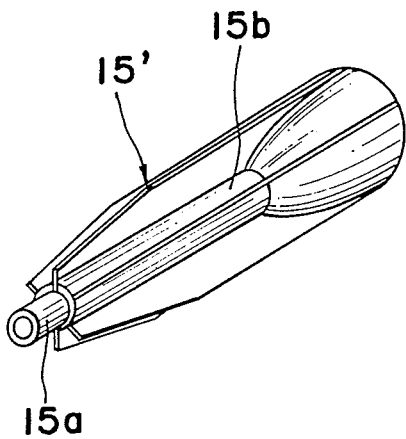
FIG. 9 is a perspective view of a body of the guide member in FIG. 8.

The guide member 15 can be produced in a variety of shapes, provided that the guide member is loaded into the lumen of the barrel 3 smoothly and fits into the tip shape of the lumen of the barrel 3. For example, the guide member 15 may be a piece of body which decreases gradually in diameter so that it assumes an elliptical cone as shown in FIG. 7. Also, the guide member 15 may be provided in the outside wall of its main part (indicated by a reference symbol d in FIG. 5) with several grooves, for example, four or eight grooves 18 extending in the direction parallel to the axis of the guide member 15 as shown in FIGS. 8 and 9, or with a circular groove. If the front end of the barrel 3 is formed by a flat wall having a nozzle, the guide member is produced in the form of a cylinder having a guide hole. Further, the tapered guide portion 17 of the guide hole may be replaced with the one formed by an elliptic paraboloid as shown in FIG. 7.

Figure 6:
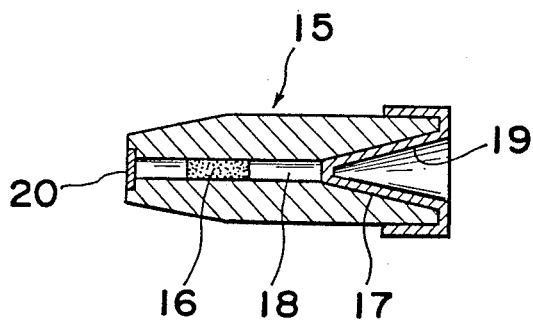

When the guide member 15 is used as a capsule for a solid or semisolid preparation, one or more solid or semisolid preparations 16 are loaded into the lumen 18 of the guide member 15, which is then sealed by a sealing means, i.e., a cap 19 and a sealing film 20, as shown in FIG. 6, to prevent the preparation 16 from discharging and to protect the same from any form of contamination. The cap 19 is removably attached to the rear end of the guide member 15, while the film 20 is attached to the tip end of the guide member. This guide member of guide capsule 15 makes it possible to aseptically perform subcutaneous implantation of the preparation.

As a material for the guide member or guide capsule, there may be used any material provided that it causes no interaction with the preparations. It is, however, preferred to use a transparent synthetic resin. Such a transparent resin includes, without being limited to polyethylene, polypropylene, polystylene, aclyronitrile-butadiene-stylene copolymers and silicones.

The cap 19 is so shaped that it may be fitted to the tapered guide portion 17 of the guide member 15 and engaged with the outside wall of the guide member 15 to prevent it from separation during transportation. As a material for the cap, there may be used any of the materials used for guide member. It should be noted that the cap 19 is not necessarily made of the same material with the guide member 15.

The film 20 is of biocompatible material, which meets requirements to ensure aseptic protection of solid preparations and to be fractured easily at a light load given by the small-sized rod portion 7 of the plunger 2. Such a biocompatible material includes, without being limited to, gelatin, collagen, starch, cellulose, albumin, silicone and the like. Also, elastic materials such as natural rubbers, silicone rubbers may be used as a material for membrane, provided that the film has a cut in the form of cross or asterisk.

The film 20 may be attached to the guide member 15, using a suitable adhesive or fixing member. If the guide member 15 has no means for supporting the film 20 as shown in FIG. 6, it is preferred to fit the film 20 to the tip of guide member 3 with an adhesive. If the guide member 15 is provided with a projection 15a at the tip end as shown in FIGS. 8 and 9, the film 20 is sandwiched by the tip end of the guide member 15 and a hold-down ring 23 used as a supporting means.

For the solid or semisolid preparation 16 there is no specific limitation, but the preparation is generally composed of one or more active ingredients, or one or more active ingredients and at least one component selected from the group of carriers and additives used as needed.

As the active ingredients, there may be used any of the conventionally known active ingredients, which include, without being limited to, interferon, interleukin, tumor necrosis factor, mitomycin, adriamycin, 5-fluorouracil, prostaglandin, prostacyclin, taspamin, hormones, hormone releasing factors. The carrier includes, without being limited to, proteins such as collagen, gelatin, albumin; biologically catabolic materials represented by synthetic polymers such as polyglycolic acid, polylactic acid, polyglutamic acid; and silicones which are catabolic with the biological structure.

The solid preparation may be produced in a variety of shapes, for example, in the form of a rod, needle, globule, disk and the like. For rod-shaped solid preparations, a preferred diameter ranges from 0.25 to 2.5 mm and the length is 3.0 to 50 mm. For globular solid preparations, a preferred diameter ranges from 0.25 to 2.5 mm.

The injector 1 of the present invention may be used in combination with any of the guide members 15 shown in any one of FIGS. 5 to 9 to allow the small-sized rod portion of the plunger to smoothly enter into the lumen of the needle member. One or more solid preparations to be implanted into the subcutaneous layers of a patient is preferably contained in the guide capsule and/or the hollow needle member.

Figure 3:
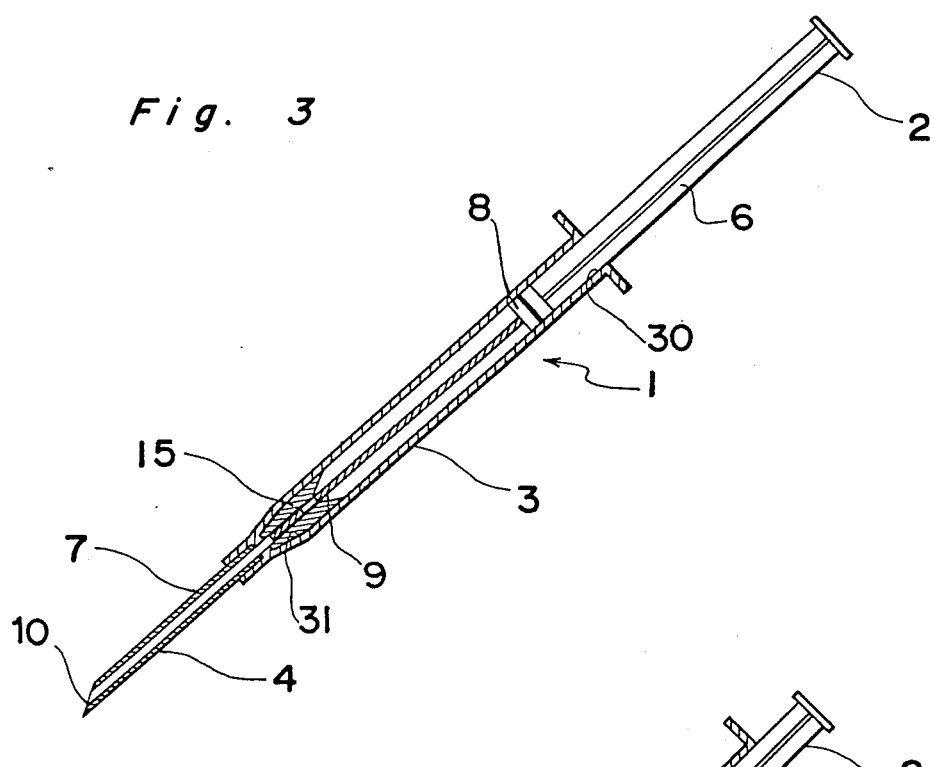
FIG. 3 is a perspective view of the injector of FIG. 1 with a guide member containing a solid preparation and being loaded therein.

In use, the plunger 2 is first removed from the barrel 1 and then the guide member 15 is loaded into the barrel 3 so that its tapered tip end goes ahead. If the guide member 15 is a guide capsule containing the solid or semisolid preparation 16 as shown in FIG. 6, the guide capsule 15 is loaded into the barrel 3 after removal of the cap 19. The plunger 2 is then inserted in the lumen of the barrel 3 and moved forwardly until the tip end of the small-sized rod portion 7 comes into contact with the guide member 15, as shown in FIG. 3. At that time, the guide capsule 15 is in the condition such that its tapered front portion is in contact with the tapered inner wall of the barrel 3.

Figure 4:
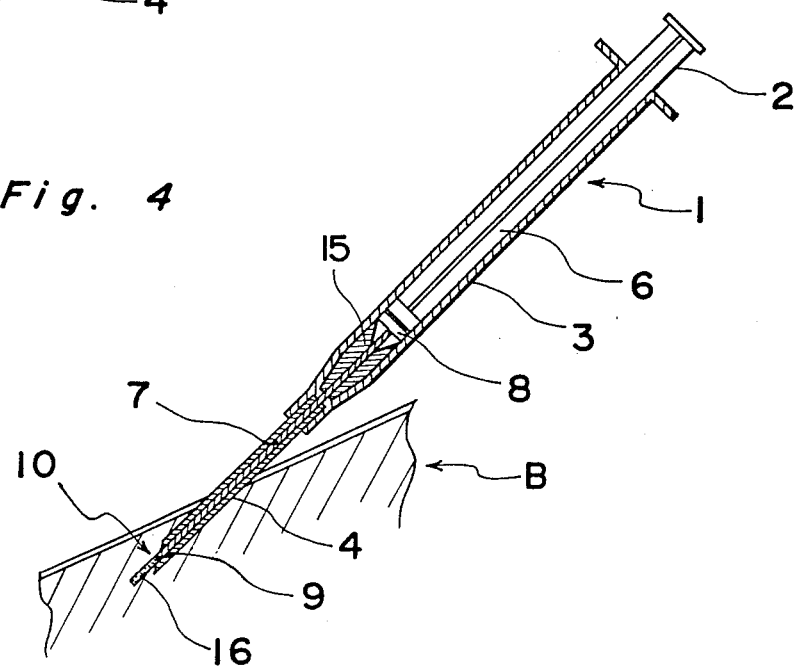
FIG. 4 is a section view of the injector of FIG. 1 in the operated condition.

After inserting the plunger to a suitable position in the barrel 3, the pointed end of the needle 4 is stabbed into the subcutaneous layers of a patient to be treated (indicated by the reference symbol B in FIG. 4) and the plunger 2 is further forced into the barrel 3 until the tip end of the large-sized slide portion 8 comes into contact with the rear end of the guide capsule 15. During this step, the solid preparation 16 is pressed into the lumen of the needle 4 by the small-sized rod portion 7 of the plunger 2 and then implanted into the subcutaneous layers (B) of the patient. When the tip end of the large-sized slide portion 8 of the plunger 2 comes into contact with the rear end of the guide member 15, the tip end 9 of the small-sized rod portion 7 of the plunger 2 is stopped in the area within the edge portion 10 of the needle 4 since the length of the small-sized rod portion 7 is determined in consideration for the lengths of the guide member 15, nozzle 5 and needle 4, and a distance between the tip end of the guide member 15 and the rear end of the needle 4. Thus, the solid preparation is implanted in the subcutaneous layers certainly without causing protrusion of the small-sized rod portion beyond the edge 10 of the needle 4.

The combined use of the needle and guide member each containing the same or different solid preparation makes it possible to implant the solid preparations at one time.

As will be understood from the above, the device of the present invention makes it possible to implant the solid preparations into the subcutaneous layers of the patient certainly and smoothly without causing extra damage to the organism. The combined use of the device and the guide member containing solid or semisolid preparations makes it possible to aseptically administer the preparations in the subcutaneous layers of the patient. Further, the combined use of the device, the needle containing a solid preparation and the guide capsule containing a solid preparation makes it possible to perform subcutaneous implantation of two or more preparations which are the same or different each other.

The invention being thus described, it will be obvious that the same may be varied in many ways. Such variations, as might readily occur to those skilled in the art, are not to be regarded as a departure from the spirit and scope of the invention, and all such modifications are intended to be included within the scope of the following claims.

What is claimed is:

1. A device for subcutaneously administering a solid or semisolid preparation in an organism, which comprises a solid preparation injector and a guide member containing one or more solid preparations and being loaded with said injector,
said solid preparation injector comprising a needle member with a pointed end, a barrel having a nozzle for attachment of said needle member, and a plunger slidably arranged in said barrel, said barrel having a front and rear end and having a lumen tapered at said front end to provide a seat for said guide member, said plunger comprising a plunger body and an elongated small-sized rod portion being connected at one end to the tip of said plunger body, said small-sized rod portion having an outside diameter equal to or smaller than the inside diameter of said needle member with the length of said small-sized rod portion being determined such that said tip of said small-sized rod portion is stopped within said pointed end of said needle member when said plunger is forced into said barrel loaded with said guide member until said plunger stops, said guide member having an outside diameter slightly smaller than the inner diameter of said barrel and having a guide hole for guiding said small-sized rod portion in said lumen of said needle member, said solid preparations being contained in said guide hole of said guide member.

2. The device according to claim 1 wherein said needle is provided with an air hole for discharging air in the barrel and the needle.

3. The device according to claim 1 wherein said barrel is of a transparent synthetic resin.

4. The device according to claim 1 wherein the needle is a cylindrical hollow tube with no hub and has an outside diameter equal to the inside diameter of the nozzle of the barrel, and wherein the needle is being fixed in the nozzle of the barrel with adhesive.

5. The device according to claim 1 wherein the needle consists of a cylindrical hollow tube and a hub mounted on the base of the tube, said tube having an inside diameter equal to that of the nozzle of the barrel.

6. The device according to claim 1 wherein the guide member is tapered at its front part to fit within said seat.

7. The device according to claim 6 wherein the guide hole of the guide member is sealed by a cap removably mounted on the rear end of the guide member and a film of an biocompatible material fixed to the tip end of the guide member.

8. The device according to claim 1 wherein said guide hole of said guide member has an outside diameter slightly smaller than the inner diameter of said barrel, and wherein said guide hole includes a tapered guide way and an elongated straight hole extending from the small end of said tapered guide way to the tip of said guide member.

9. A device for subcutaneously administering a solid or semisolid preparation in an organism which comprises a hollow needle member, a barrel having a lumen and a nozzle for attachment of said needle member, a plunger slidably arranged in said barrel, and a guide member snugly accommodated within said lumen of said barrel and in contact with the front inner wall of said barrel,
said plunger comprising a plunger body having an outside diameter equal to or slightly smaller than the inside diameter of said barrel and an elongated small-sized rod portion having an outside diameter equal to or slightly smaller than the inside diameter of said needle, said smaller rod portion being connected to the tip of said plunger and having a length equal to or slightly smaller than a distance from the rear end of said guide member to the tip of said needle member,
said guide member having an outside diameter slightly smaller than the inside diameter of said barrel and being provided with a funnel-shaped guide hole to guide said small-sized rod portion of said plunger, said guide hole of said guide member containing at least one solid preparation.

10. A guide member for use in a device for subcutaneous implantation of a solid preparation comprising a hollow cylindrical barrel, a plunger slidably arranged in said barrel, and a hollow needle member attached to said barrel, said guide member comprising a cylindrical body with an outside diameter slightly smaller than the inner diameter of said barrel, and having a guide hole composed of a tapered guide portion having a small end and an elongated straight portion extending from the small end of said tapered portion to the tip of said guide member, and wherein said guide member is tapered at its front part to fit within the tapered front inner wall of the barrel, and wherein said guide hole of said guide member is sealed by a cap removably mounted on the rear end of said guide member and a film of a biocompatible material fixed to the tip end of said guide member.

11. The guide member according to claim 10 wherein said guide member contains at least one of said preparation in said guide hole.

12. A device for subcutaneously administering a solid or semisolid preparation in an organism, comprising a hollow needle member containing at least one solid preparation, a barrel having a lumen and a nozzle for attachment of said needle member, a plunger slidably arranged in said barrel, and a guide member snugly accommodated within said lumen of said barrel and to be in contact with the front inner wall of said barrel, said plunger comprising a plunger body having an outside diameter equal to or slightly smaller than the inside diameter of said barrel and an elongated small-sized rod portion having an outside diameter equal to or slightly smaller than the inside diameter of said needle, said small-sized rod portion being connected to the tip of the plunger body and having a length equal to or slightly smaller than a distance from the rear end of said guide member to the tip of said needle member.

* * * * *